US00PP10394P

United States Patent [19]

Plate

[11] Patent Number: Plant 10,394

[45] Date of Patent: May 12, 1998

[54] PHALAENOPSIS ORCHID PLANT NAMED 'SYLBA'

[75] Inventor: Renate Plate, Bremen, Germany

[73] Assignee: Wolfgang Bock Pflanzenexport KG, Bremen, Germany

[21] Appl. No.: 762,798

[22] Filed: Dec. 9, 1996

[51] Int. Cl.[6] ..... A01H 5/00

[52] U.S. Cl. ..... Plt./87.3

[58] Field of Search ..... Plt./87.3

*Primary Examiner*—James R. Feyrer
*Assistant Examiner*—Elizabeth C. Kemmerer
*Attorney, Agent, or Firm*—Foley & Lardner

[57] ABSTRACT

A new and distinct Phalaenopsis orchid plant named 'Sylba,' particularly characterized by its attractive white flowers with fine lavender stripes and a dark red-purple spotted center, economical propagation via tissue culture, very rapid growth, and plant dimensions suitable for packaging and shipping to market.

2 Drawing Sheets

1

The present invention comprises a new and distinct cultivar of Phalaenopsis, a genus in the family Orchidaceae, referred to by the cultivar 'Sylba'. The new cultivar is a hybrid selected from the progeny of a cross of parent plants identified below.

Phalaenopsis comprise a genus of about 55 species of herbaceous perennials many of which, or the hybrids thereof, are suitable for cultivation in the home or greenhouse. Phalaenopsis are predominantly epiphytic or rock-dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

Phalaenopsis orchids, often referred to as 'Moth Orchids' in the horticultural trade, are frequently used to furnish cut flowers for the florist trade, or sold as flowering potted plants for home or interiorscope.

Phalaenopsis produce upright or pendent lateral racemes, often with many showy flowers which open in succession beginning with the lowermost. The flowers possess three sepals and three petals, the lateral ones being alike. The lowermost petal, called the labellum, is three lobed and is often more brightly colored than the other flower segments. Flower colors include various shades of pink, white, yellow and red-brown.

Phalaenopsis orchids are typically propagated from seeds. Asexual propagation of Phalaenopsis is often done from off-shoots which frequently arise from the lower bracts of the inflorescence. The resulting plants are detached from the mother plant and may be planted in a suitable substrate. Asexual propagation of Phalaenopsis through the use of tissue culture, though feasible, is not widely practiced because it is often relatively inefficient and costly as currently applied.

The new cultivar is a product of a breeding program carried out by the inventor Renate Plate, in Bremen, Germany. The new cultivar 'Sylba' is a result of a cross of selected, but unnamed parentage made in Freie Hansestadt, Bremen, Germany, in 1984. The new cultivar was discovered from the progeny of the stated cross in Bremen, Germany, by inventor Renate Plate on Sep. 3, 1986. Asexual propagation of the new cultivar by tissue culture done under the supervision of the inventor in Bremen, Germany was used to increase the number of plants for evaluation and has demonstrated the stability of the combination of characteristics from generation to generation.

The following observations, measurements and values

2 describe plants grown in Lithia, Fla. under greenhouse conditions which closely approximate those generally used in horticultural practice.

The following traits have been repeatedly observed to be characteristics which in combination distinguish Sylba from generally available seedling-derived Phalaenopsis common in commercial cultivation.

1. The flowers produced by 'Sylba' are white with fine lavender pink stripes and a dark red-purple spotted center.

2. The inflorescence produced by Sylba is short, very sturdy and easily staked and packaged for shipping.

3. Plants of 'Sylba' grow quickly and begin flowering early, producing marketable flowering plants in approximately 9–11 months.

4. Plants of 'Sylba' may be propagated economically and uniformly using tissue culture.

Commercially available seedling-derived Phalaenopsis are heterogeneous genetically, and typically lack uniformly in growth, vigor, habit, and flower quality. Because of these inconsistent characteristics, a direct comparison for 'Sylba,' whose combined characteristics are uniform and predictable, is not available.

All color references are measured against The Royal Horticultural Society Colour Chart (R.H.S.). Colors are approximate as color depends on horticultural practices such as light level and fertilization rate, among others, without, however, any change in genotype.

In the accompanying color photographic drawings, the photograph on Sheet 1 comprises a top perspective view of the inflorescence and foliage of a plant of Sylba in a 20 cm pot.

The photograph on Sheet 2 is a close up view of the flowers.

The photographs were taken approximately 12 months after planting a 16 week old liner obtained by tissue culture and grown under approximate growing conditions. Colors are as accurate as possible with color illustrations of this type.

Origin: Seedling from a cross of selected but unnamed parentage.

Classification: Phalaenopsis hybrid, cv. Sylba.

Propagation: Asexual propagation by tissue culture.

Inflorescence:

*Flower description.*—The sepals and petals are white with fine lavender pink stripes along the veins, and dark pink speckles. The lateral (lower) sepals are boldly spotted with dark red-purple. The sepals are elliptic-ovate in shape, the lateral petals are broadly ovate with a rounded apex. The sepals and petals are distinctly cupped. The labellum is deeply three-lobed with two prominent callosities at the central junction of the lateral lobes and base of the midlobe. The lateral lobes of the labellum fold upward about the column, the midlobe extends forward and is terminated by two twisted filiform appendages at the apex. The lateral lobes of the labellum are obovate in shape, the midlobe is triangular. The labellum is white in base color with bold spots and stripes of dark red-purple. The two callosities are yellow with minute dark red-purple spots and stripes. The margins of the labellum are tinged with yellow.

*Dimension.*—Overall: Approximately 8.5 cm to 8.8 cm wide, and 7.6 to 8.0 in height. Sepals: Approximately 3.9 to cm 4.2 cm long, and 2.8 cm to 3.0 cm wide. Petals: Approximately 4.0 cm to 4.3 cm long, and 4.9 cm to 5.3 cm wide. Labellum: Approximately 2.9 cm to 3.1 cm long, and 2.5 cm wide (not flattened).

*Flower color.*—Sepals: Adaxial surface: 155 D tinged with 76 D, with 87 C stripes, and 72 B speckles. Lower sepals also boldly spotted with 59 B. Abaxial surface: 69 C-D, with 87 C streaks. Lateral Petals: Adaxial surface: 155 D tinged with 76 D, with 87 C stripes, and 72 B speckles. Abaxial surface: 155 D tinged with 76 D, with 87 C stripes. Labellum: Adaxial surface: Base color white 155 D, boldly striped and speckled with 60 A and 70 A. Callosities 155 A, 13 C, striped and speckled with 60 A. Margin tinged with 13 C. Abaxial surface: 155 D, speckled with 72 A-B, with 13 C margin. Raceme: Dimension: The raceme is typically staked upright to a height of approximately 53 cm. The raceme is approximately 75 cm from base to tip, and 0.6 cm in diameter at its midpoint. The color of the raceme is 200 A, tinged with 147 A.

*Flowering time.*—For an untreated plant as depicted in the photograph on Sheet 1, (which is flowering for the second time), 8–10 flowers/unopened buds are present. First flowers can be expected approximately 4–6 months after planting a 16 week old liner, approximately 3–5 flowers in number.

Reproductive organs: The stamens, style and stigmas are fused into a single short structure called the column, possessing one terminal anther with pollen grains united into a pollinia, which are covered by an anther cap. The stigma is located under the column behind the pollinia. Ovary inferior, three carples present.

*Column.*—The column is approximately 1 cm long, 6 mm wide, and is 155 D in color with areas of 78 B-C.

*Pollinia.*—Two, 1.0 mm oval masses of pollen present, 23 B in color.

*Stigma.*—Concave, sticky and round 5 mm area under column, 155 D in color.

*Ovary.*—14 mm long, 3 mm diameter, color 84 C. Pedicel approximately 2.7 cm long, 3.5 mm diameter, 145 B-C in color.

General appearance: Under appropriate growing conditions, plants of 'Sylba' attain a mature size of approximately 10.0 cm to 12 cm in height and approximately 43.5 cm to 48 cm in width.

Leaves:

*Form.*—The leaf blade is long and elliptic with an obtuse to slightly retuse apex and a cuneate base. The margins are entire. The midrib is straight over the length of the leaf. The leaf blade is flat or slightly folded upward from the midrib. The upper leaf is slightly glossy, more so on newly emerged leaves. The leaves are leathery, and thick.

*Size.*—Leaf blades of a mature sized plant are approximately 21 cm to 25 cm in length and approximately 8.3 cm to 9.4 cm in width.

*Veins.*—Veins are sunken, within the thick leaf blade.

*Color.*—Adaxial surface: Darker and greener than, but closest to, 137 A. Abaxial surface: 146 A-B, frequently with small speckles of anthiocyanous 59 A along the leaf margin.

Roots: Very thick greenish white fleshy roots.

General Observations

Phalaenopsis 'Sylba' produces flowers which are white having fine lavender pink stripes, and a contrasting dark red-purple spotted center. The inflorescence is strong and easily packaged for shipping. The plant grows very quickly to marketable size. Sylba can be economically propagated via tissue culture.

I claim:

1. A new and distinct cultivar of Phalaenopsis Orchid plant named 'Sylba,' as illustrated and described.

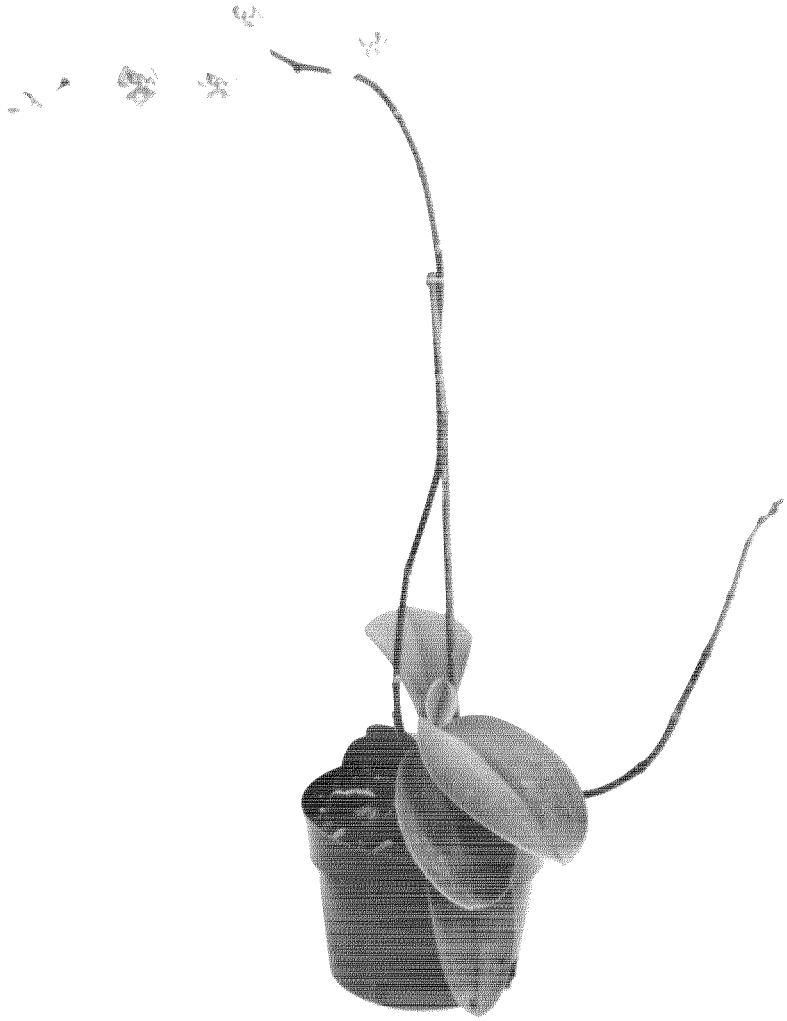

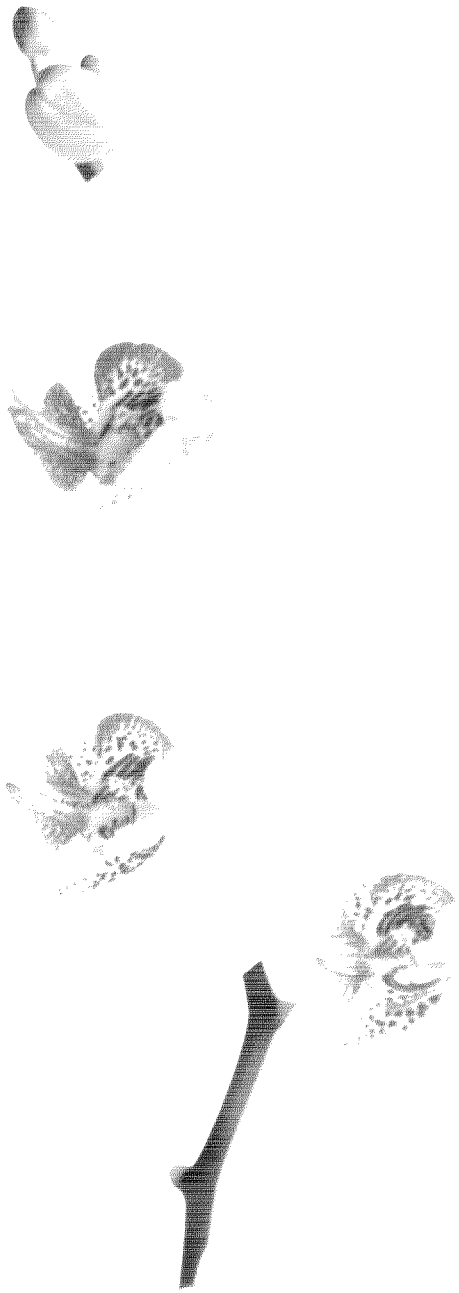

* * * * *